United States Patent [19]

Frazin et al.

[11] Patent Number: 5,394,878
[45] Date of Patent: Mar. 7, 1995

[54] METHOD FOR TWO DIMENSIONAL REAL TIME COLOR DOPPLER ULTRASOUND IMAGING OF BODILY STRUCTURES THROUGH THE GASTRO INTESTINAL WALL

[76] Inventors: Leon J. Frazin, 2106 N. Dayton, Chicago, Ill. 60614; Mohammed N. Siddiqui, 4215 Whitebirch Dr., Lisle, Ill. 60532

[21] Appl. No.: 243,614

[22] Filed: May 16, 1994

Related U.S. Application Data

[63] Continuation of Ser. No. 90,785, Jul. 13, 1993, abandoned.

[51] Int. Cl.⁶ ................................. A61B 8/12
[52] U.S. Cl. ................................. 128/662.06
[58] Field of Search ............ 128/660.01, 660.05, 128/661.08, 661.09, 662.03, 662.05, 662.06, 4; 73/625

[56] References Cited

U.S. PATENT DOCUMENTS

| | | | |
|---|---|---|---|
| 4,344,159 | 8/1982 | Ballinger | 73/625 |
| 4,375,818 | 3/1983 | Suwaki et al. | 128/4 |
| 4,582,067 | 4/1986 | Silverstein et al. | 128/662.06 |
| 4,819,650 | 4/1989 | Goldstein | 128/662.06 |
| 5,022,399 | 6/1991 | Biegeleisen | 128/662.06 |
| 5,025,778 | 6/1991 | Silverstein et al. | 128/4 |
| 5,054,491 | 10/1991 | Saito et al. | 128/662.06 |
| 5,207,225 | 5/1993 | Oaks et al. | 128/662.06 |

*Primary Examiner*—George Manuel
*Attorney, Agent, or Firm*—Welsh & Katz, Ltd.

[57] ABSTRACT

This invention is for a new device and method for 2 dimensional, real time ultrasonic imaging of deep internal organs and vascular structures. This device and method allows clear unattenuated images of these organs and vessel by placing a 2 dimensional, real time ultrasonic transducer immediately adjacent the organ or vessel by introduction of the transducer, on the end of probe, into either the colon or the esophogus. The transducer can then be positioned adjacent the organ or vessel of interest of imaging.

14 Claims, 1 Drawing Sheet

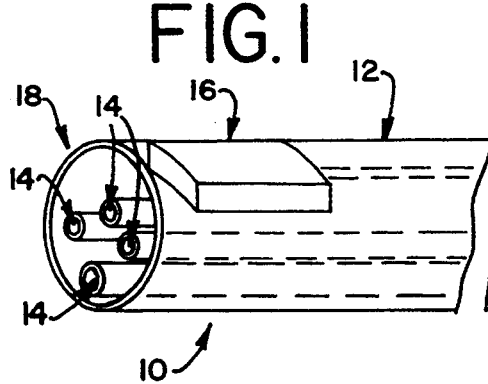
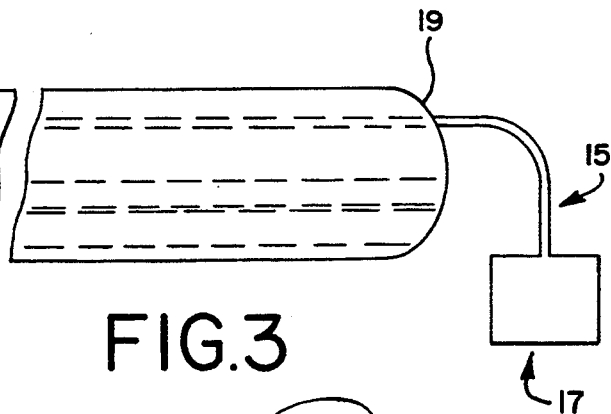
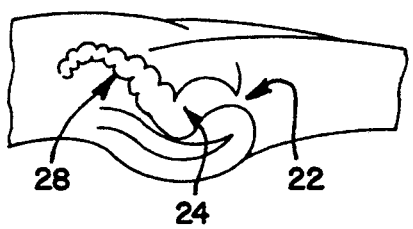
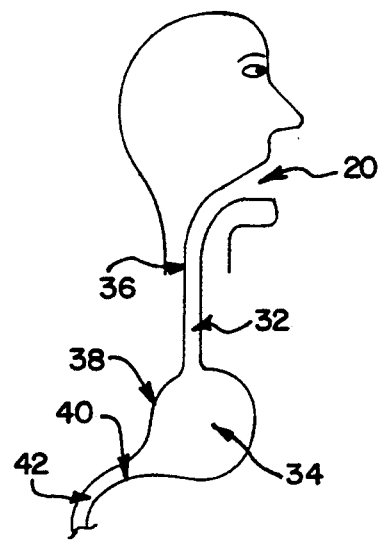
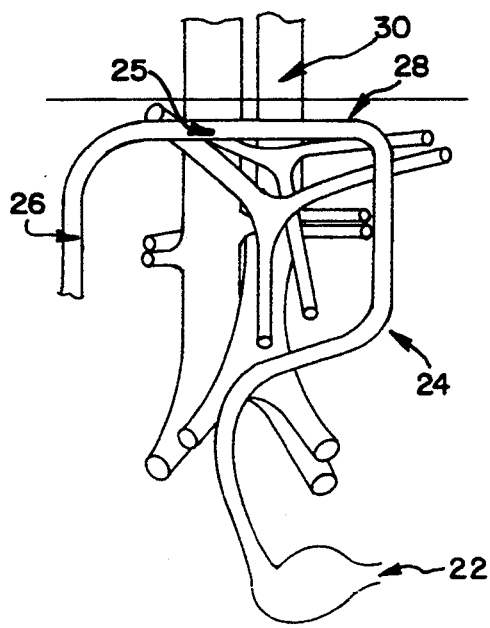
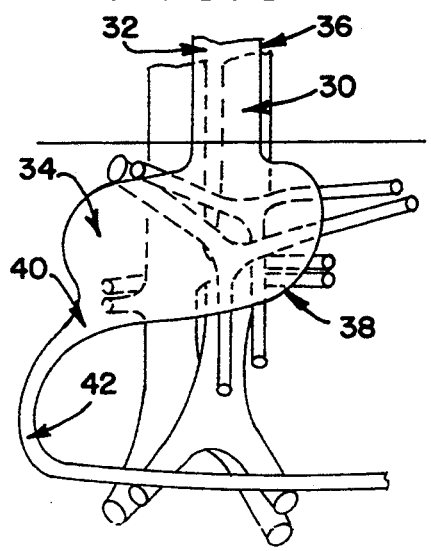

METHOD FOR TWO DIMENSIONAL REAL TIME COLOR DOPPLER ULTRASOUND IMAGING OF BODILY STRUCTURES THROUGH THE GASTRO INTESTINAL WALL

This application is a continuation of application Ser. No. 08/090,785, filed Jul. 13, 1993, now abandoned.

The present invention relates to a method and apparatus for imaging internal structures through the use of a two dimensional real time color Doppler ultrasonic transducer located on one end of a probe which is inserted into the body through the mouth or rectum. The method and apparatus of this invention provide clear and unattenuated images of internal organs and vascular structure, even though they lie deep within the body.

BACKGROUND OF THE INVENTION

The diagnostic capabilities of the medical profession have increased significantly throughout the years. One such advancement has been the use of ultrasound to obtain images of internal organs. The ultrasonic waves reflect off of the interfaces of the organs to provide a two dimensional image of the organ on a CRT viewing screen. Ultrasound transducers can be either static, which provide a stationary image, or two dimensional, which provide a moving or real time image. Computerized three dimensional reconstruction of ultrasonic imaging is also possible.

Other uses for ultrasound include the ability to determine flow rate and direction of fluid within vessels of the body. A Doppler ultrasound transducer, combined with a two dimensional transducer is used to determine flow rate and direction. The Doppler transducer, either a pulse or continuous flow Doppler transducer, allows the rate and direction at which blood or other fluids are moving through the veins, arteries or portal vessels of the body to be measured. Color coding of Doppler interrogation is also possible. This information can be used to diagnose blockages or restrictions within the vessel.

The use of ultrasound allows the character and status of certain internal organs and vascular structures to be determined through the use of non-invasive, non-surgical procedures. Two dimensional, real time, transducers provide more information regarding the functioning of certain organs than static transducers and are, therefore, more useful from a diagnostic view point than static transducers.

Ultrasound images are produced by the ultrasound waves reflecting off the surface of soft tissues in the body. Ultrasound waves can penetrate to varying depths, before being deflected. The depth is determined by the frequency at which the transducer transmits the sound waves. Not all waves are reflected however, some pass through the tissue and others are absorbed by the tissue. Since the image is created by the pattern of the reflected waves, the more waves that are reflected, the clearer the image produced will be.

In general, abdominal ultrasonic examinations are conducted with the ultrasound transducer being placed on the outside of the abdominal wall. If the organ to be imaged is close to the surface, it is generally not difficult to obtain a good quality image. However, as the structure of interest lies deeper within the body, or if the patient is overweight or if bowel gas is present the image produced will not be as clear due to absorption of waves by the intervening tissue.

The farther away from the transducer that the organ lies, the fewer waves will reach it and the image will be less and less clear. In addition, if the organ or vessel is shielded, lying behind other organs, the image can also be distorted due the reflection of waves off the intervening tissue, causing tissue imposed attenuation of the image.

These problems cannot be solved by placing the transducer on the patient's back due to the existence of too much bone and muscle tissue, through which the ultrasound waves cannot penetrate.

Other options for use of ultrasound technology include the placement of a static ultrasound transducer on a flexible probe for insertion into the stomach or colon. The static transducer is used to obtain a still picture of the colon, pancreas, biliary tract or esophagus wall. This technique is generally used to obtain images of ulcers, lesions, or tumors on the walls or within the structures.

Doppler transducers are also used as a guiding means on the end of a catheter. The direction of blood flow is determined and used to guide the catheter into the correct blood vessel. Once in position, the required procedure can take place.

None of these procedures provide an apparatus or a method for the two dimensional imaging of the deep or shielded internal organs, or the detection of the flow rate and direction in deep or shielded blood vessels, such as the abdominal aorta and its branches.

There exists, therefore, a need for obtaining high resolution, dynamic imaging of the internal structures lying deep within the body and for obtaining accurate flow rate and direction of vessels which lie deep in the body or which are blocked by organs.

SUMMARY OF THE INVENTION

It is an object of this invention to provide an apparatus and a method for overcoming the problems associated with the two dimensional imaging of abdominal structures, by allowing the two dimensional real time imaging of deep internal abdominal structures, as well as the internal structures of obese patients or patients with bowel gas, with increased clarity and precision. In addition, structures previously impossible to image with transabdominal imaging techniques can now be imaged.

It is a further object to allow the detection of flow rate and direction of the veins and arteries in the abdominal area with increased accuracy. These objects are obtained by using the apparatus and method of this invention which allows insertion of a flexible probe containing a two dimensional real time ultrasonic transducer (also known as a sector array) into a body cavity, such as the rectum or mouth. The two dimensional transducer is then positioned adjacent to the organ or vessel to be imaged. In this way, the ultrasound transducer is placed very close, if not immediately adjacent to the organ or vessel to be imaged and tissue attenuation or absorption of the ultrasound waves is largely eliminated.

Flow rate and direction of fluid within a vessel can also be determined by the same method through the use of a two dimensional real time Doppler ultrasound transducer. The rate and direction readings obtained are more accurate due to the proximity of the transducer to the vessel of interest.

There are a variety of two dimensional real time transducers that can be used, including mono and biplane as well as a rotatable monoplane, which becomes an omniplanar transducer. In addition, if desired, a biplane matrix can be employed. The matrix design can also be made to rotate, creating an omniplane matrix. The transducer chosen will depend upon the structure to be imaged as well as the information sought.

The device used to perform the method of this invention comprises a flexible probe having a plurality of internal lumens and a two dimensional ultrasound transducer positioned on the side, near the distal end of the probe.

The lumens contained in the probe can be used to house several different instruments. In general, there will be a guiding means to aid in placement of the transducer and a means for introducing and removing fluid into the colon, or into the esophagus, stomach or duodenum. These can also be various instruments lumens, if a specific procedure, in addition to imaging, is to be performed The guiding means can include a light source as well as fiber optics for visually guiding the catheter. There may also be a mechanical guiding means for manipulation of the tip of the probe, allowing proper placement of the transducer against the wall of the colon, stomach or duodenum. The mechanical guiding means will also allow manipulation of the colon or stomach in any direction to obtain images of different organs, or different locations of an organ or vessel.

A means for introducing fluid into the stomach, colon, or duodenum as well as a suction apparatus for removal of the fluid and debris from these structures is generally present. The fluid is used to wash debris from the area of interest and will also provide a fluid interface between the transducer and the colon or esophagus wall. The addition of fluid can also be used to distend the colon, stomach or duodenum, causing it to bump against nearby organs, thereby decreasing the space between them. This will result in improved imaging of the organ.

Other lumens can be used for the introduction of various instruments that may be used during the imaging procedure.

In one embodiment, the probe containing the selected transducer is inserted into the rectum and then guided through the descending, transverse and ascending colon until it is in a position near the organ of interest. The colon can then be manipulated by controls on the handle of the probe and/or applying manual pressure on the abdomen. This allows the positioning of the transducer adjacent to a particular organ or vessel of interest or even adjacent a specific area of an organ or vessel. The location of the transducer in relation to the outside organs can be determined by the image viewed on the screen. This procedure allows certain specific organs to be imaged as well as a particular section of an organ to be imaged. In the case of blood vessels, such as the abdominal aorta and its branches, various sections of the vessel can be imaged to locate possible plaques, blockages or restrictions.

Alternatively, the transducer can be inserted into the mouth and then into the esophagus, stomach or duodenum of the patient, allowing the imaging of adjacent structures. If a particularly small probe and transducer is used, it can be passed through the pyloric end of the stomach and then into the duodenum for imaging of additional structures.

By positioning the transducer in either the colon, stomach or duodenum, the distance the ultrasound waves must travel prior to contacting the organ of interest is greatly reduced. In addition, there will not be any other organs between the transducer and the organ or vessel of interest, except for the gastrointestinal wall or esophagus, stomach, or duodenum, which is being imaged through. Although this method is more invasive than ultrasonic imaging from outside the body, it still does not require a surgical procedure and provides greatly superior results. In many cases this procedure can be conducted on an outpatient basis.

BRIEF DESCRIPTION OF THE DRAWINGS

FIG. 1 is a perspective view of the probe device.

FIG. 2 is an anatomical drawing showing insertion of the device into the rectum;

FIG. 3 is an anatomical drawing showing insertion of the device into the mouth;

FIG. 4 is a plan view of certain internal structures showing the relative location of these structures and the colon;

FIG. 5 is a plan view of certain internal structures showing the relative placement of these structures and the esophagus, stomach, and duodenum.

DETAILED DESCRIPTION OF THE INVENTION

As shown in FIG. 1, the device 10 for conducting the method of this invention consists of a probe 12 with multiple lumens 14 and a two dimensional real time ultrasonic transducer 16. The transducer is located near the distal end 18 of the probe 12 and is positioned to one side of the probe 12. The transducer 16 is connected to an imaging display device 17 by a cable 15 that passes through the probe 12 and out the proximal end 19.

The distal end 18 of the probe 12 is inserted into either the mouth 20 (FIG. 3) or the rectum 22 (FIG. 2) of the patient. Where the probe 12 is inserted is determined by the structure to be imaged.

When the probe 12 is inserted into the rectum 22, it is then guided through the colon 24 until the distal end 18 is positioned near to the structure to be imaged. When the distal end 18 of the probe 12 is adjacent to the structure to be imaged, the transducer 16 is placed against the wall 28 of the colon 24 and the two dimensional transducer 16 and image display device 17 are activated.

If the aorta 30 (FIGS. 4 and 5) or certain other abdominal veins, arteries, or solid organs are to be viewed, then the transducer 16 is moved through the colon 24 until the distal end 18 reaches the transverse colon 25 or even the ascending colon 26. The colon 24 can then be manipulated and moved up, down, right, left or any direction to alter the exact location of the artery, vein or other structure being viewed. In this way, blockages of the artery or vein can be located with greater precision.

The lumens 14 can contain several different apparatus depending upon the procedure being performed. In general one lumen will contain a light and fiber optic device to be used for visually positioning the distal end 18 of the probe 12. In addition, the probe 12 can be guided to the correct position by activating the transducer 16 and viewing the image on the image display device 17. The image will determine where in the body the tranducer is located.

In addition to a visual guiding means, one lumen 14 can contain a mechanical guiding means for manipulation of the colon 24. This guiding means is controlled by the handle (not shown) of the probe 12. Another lumen can contain a source for introduction of fluid into the colon 24. This fluid is used to flush the colon and to aid in obtaining a fluid interface between the transducer 16 and the colon wall 28. Pumping fluid into the colon 24 can also result in distention of the colon 24 so that is pushes up against the neighboring organs. This will reduce the distance between the transducer 16 and the organ to be viewed.

If desired, other lumens can used for various instruments, if procedures other than imaging will take place. These instruments will be controlled by the handle of the probe 12.

When the distal end 18 of the probe 12 is inserted into the mouth 20, it is guided through the esophagus 32 until it is positioned adjacent to the organ or vessel to be viewed. Additional organs and vessels can be viewed if the probe 12 is passed through the esophagus 32 into the stomach 34. Once correctly positioned, the transducer 16 is placed against the esophagus wall 36 or the stomach wall 38 and activated.

Additional structures can be viewed if the distal end 18 of the probe 16 is passed through the pyloric end 40 of the stomach 34 and into the duodenum 42.

Flow rate and direction of vessels can also be determined by the use of Doppler in either pulse or continuous mode. Color representation of Doppler flow velocity and direction can also be obtained.

Although the present invention has been described with preferred embodiments illustrated herein, it is to be understood that other modifications and variations may be resorted to without departing from the spirit and the scope of the present invention. Such modifications and variations are considered to be within the purview and the scope of the appended claims.

We claim:

1. A method for providing a two dimensional real time ultrasonic image of internal structures of the human body comprising the steps of:
   a. providing a probe having a first and a second end with a two dimensional real time ultrasonic transducer capable of producing two dimensional real time images at the first end thereof, with the second end of the probe including means for electrically connecting said transducer to an image display device which displays a two dimensional real time image when the two dimensional real time ultrasonic transducer is activated;
   b. inserting the first end of the probe and the two dimensional real time ultrasonic transducer into the rectum of the body and then into the colon, said colon passing adjacent to the internal structure to be imaged, said structure being located outside of the colon;
   c. visually guiding and advancing the first end of the probe through the colon into the transverse, descending, or ascending colon, and the first end of the probe is then manipulated to move the colon bringing the two dimensional real time ultrasonic transducer adjacent to the structure to be imaged, said structure being located outside of the colon; and
   activating the two dimensional real time ultrasonic transducer to provide a moving, two dimensional real time image of the internal structure for viewing on the image display device.

2. The method for ultrasonic imaging as defined in claim 1, wherein the probe is an endoscope and the two dimensional real time ultrasonic transducer is located near the first end of the endoscope, and the endoscope is used to guide the transducer to a location adjacent the structure to be imaged.

3. The method for ultrasonic imaging as defined in claim 1, wherein said two dimensional real time ultrasonic transducer is activated at a time prior to reaching a position adjacent to the structure to be imaged.

4. The method for ultrasonic imaging as defined in claim 3, wherein said two dimensional real time ultrasonic transducer is used to determine the position of the transducer relative to the organ to be viewed by monitoring the image shown on the image display device.

5. A method for providing a two dimensional real time ultrasonic image of internal structures of the human body comprising the steps of:
   a. providing a probe having a first and a second end with a two dimensional real time ultrasonic transducer, capable of producing two dimensional real time images, at the first end thereof, with the second end of the probe including means for electrically connecting said transducer to an image display device which displays an image when the two dimensional real time ultrasonic transducer is activated;
   b. inserting the first end of the probe and the two dimensional real time ultrasonic transducer into the mouth and then into the esophagus;
   c. visually guiding and advancing the first end of the probe through the esophagus and into the stomach where the transducer is placed on the stomach wall adjacent to the structure to be imaged, said structure being located outside of the stomach;
   d. activating the two dimensional real time ultrasonic transducer to provide a moving, two dimensional, real time image of the internal structure for viewing on the image display device.

6. The method for ultrasonic imaging as defined in claim 5, wherein said two dimensional real time ultrasonic transducer is visually guided through the esophagus, into the stomach and through the pyloric end of the stomach and into the duodenum, said two dimensional real time ultrasonic transducer then being placed adjacent to the structure to be imaged, said structure being located outside of the duodenum.

7. A method for determining the blood flow rate and direction in a particular blood vessel comprising the steps of:
   a. providing a probe having a first and a second end with a Doppler two dimensional real time ultrasonic transducer capable of providing both Doppler interrogation and producing two dimensional real time images, located on the first end thereof, and the second end of the probe including means for electrically connecting said transducer to an image display device;
   b. inserting the first end of the probe and the Doppler two dimensional real time transducer into the rectum and then into the colon, where the colon passes adjacent to the vessel whose flow rate and direction is to be determined, said vessel being located outside of the colon;
   c. visually guiding and advancing the first end of the probe through the colon such that the Doppler two dimensional real time ultrasonic transducer is located adjacent the vessel whose flow rate and direction is to be determined;
   d. activating said Doppler two dimensional real time ultrasonic transducer and utilizing the two dimensional real time image produced to precisely place the transducer close to the vessel whose flow rate and direction is to be determined and then using Doppler interrogation to calculate the blood flow rate and direction of the selected vessel.

8. The method for determining blood flow rate and direction as defined in claim 7 wherein said Doppler two dimensional real time ultrasonic transducer is activated at a time prior to reaching a position adjacent to the vessel whose flow rate and direction is to be determined.

9. The method for determining blood flow rate and direction as defined in claim 8, wherein said Doppler two dimensional real time ultrasonic transducer produces a two dimensional image on the image display device representing the position in the body of the Doppler two dimensional real time transducer as the transducer is guided to a position adjacent the vessel whose flow rate and direction is to be determined.

10. The method for determining blood flow rate and direction as defined in claim 7, wherein the Doppler two dimensional real time ultrasonic transducer is guided through the colon into the descending, transverse or ascending colon, and the probe is then manipulated to move the colon to bring the Doppler two dimensional real time transducer adjacent to the vessel whose flow rate and direction is to be determined, said vessel being located outside of the colon.

11. The method for determining blood flow rate and direction, as defined in claim 7, wherein the probe is an endoscope and the Doppler two dimensional real time transducer is located at the first end and one side of the endoscope.

12. The method for determining blood flow rate and direction as defined in claim 7, wherein the Doppler two dimensional real time ultrasonic transducer is inserted into the mouth; and the Doppler two dimensional real time ultrasonic transducer is guided through the esophagus until the transducer is adjacent to the vessel whose flow rate and direction is to be determined.

13. A method for determining the blood flow rate and direction in a particular blood vessel comprising the steps of:
   a. providing a probe having a first and a second end with a Doppler two dimensional real time ultrasonic transducer capable of producing both Doppler and two dimensional real time images located on the first end thereof, and the second end of the probe including means for electrically connecting said transducer to an image display device;
   b. inserting the first end of the probe and the Doppler two dimensional real time transducer into the mouth; and then into the esophagus;
   c. visually guiding and advancing the first end of the probe through the esophagus and into the stomach where the transducer is placed on the stomach wall adjacent to the vessel whose flow rate and direction is to be determined said vessel being located outside of the stomach;
   d. activating said Doppler two dimensional real time ultrasonic transducer and utilizing the two dimensional real time image produced to precisely place the transducer close to the vessel whose flow rate and direction is to be determined and calculating the blood flow rate and direction of the vessel.

14. The method for determining blood flow rate and direction as defined in claim 13, wherein the Doppler two dimensional real time ultrasonic transducer is visually guided through the esophagus, into the stomach and through the pyloric end of the stomach and into the duodenum; the Doppler two dimensional real time ultrasonic transducer then being placed adjacent to the vessel to be studied, said vessel being located outside of the duodenum.

* * * * *

UNITED STATES PATENT AND TRADEMARK OFFICE
CERTIFICATE OF CORRECTION

PATENT NO. : 5,394,878
DATED : March 7, 1995
INVENTOR(S) : Frazin, Leon J.

It is certified that error appears in the above-indentified patent and that said Letters Patent is hereby corrected as shown below:

In the abstract:

line 5, change "vessel" to -- vessels --

Column 2, line 5, insert -- to -- after "due"

Column 3, line 18, insert -- . -- after "performed"

Column 5, line 3, change "is" to -- it --

Column 5, line 7, insert -- be -- after "can"

Signed and Sealed this

Tenth Day of October, 1995

Attest:

BRUCE LEHMAN

*Attesting Officer*      *Commissioner of Patents and Trademarks*